(12) United States Patent
Dowd et al.

(10) Patent No.: US 12,122,799 B2
(45) Date of Patent: Oct. 22, 2024

(54) ANTIBIOTICS FOR VETERINARY STAPHYLOCOCCAL INFECTIONS

(71) Applicants: THE GEORGE WASHINGTON UNIVERSITY, A CONGRESSIONALLY CHARTERED NOT-FOR-PROFIT CORPORATION, Washington, DC (US); WASHINGTON UNIVERSITY, St. Louis, MO (US)

(72) Inventors: Cynthia Dowd, Washington, DC (US); Audrey Odom John, St. Louis, MO (US); Rachel Edwards, St. Louis, MO (US); Kenneth M. Heidel, Washington, DC (US); Xu Wang, Exton, PA (US); Rene Chofor, Washington, DC (US)

(73) Assignees: THE GEORGE WASHINGTON UNIVERSITY, A CONGRESSIONALLY CHARTERED NOT-FOR-PROFIT CORPORATION, Washington, DC (US); WASHINGTON UNIVERSITY, St. Louis, MO (US)

( * ) Notice: Subject to any disclaimer, the term of this patent is extended or adjusted under 35 U.S.C. 154(b) by 829 days.

(21) Appl. No.: 17/253,841

(22) PCT Filed: Jun. 18, 2019

(86) PCT No.: PCT/US2019/037761
§ 371 (c)(1),
(2) Date: Dec. 18, 2020

(87) PCT Pub. No.: WO2019/246119
PCT Pub. Date: Dec. 26, 2019

(65) Prior Publication Data
US 2021/0261580 A1 Aug. 26, 2021

Related U.S. Application Data

(60) Provisional application No. 62/686,416, filed on Jun. 18, 2018.

(51) Int. Cl.
*A61P 31/04* (2006.01)
*C07F 9/40* (2006.01)

(52) U.S. Cl.
CPC ............ *C07F 9/4015* (2013.01); *A61P 31/04* (2018.01); *C07F 9/4009* (2013.01)

(58) Field of Classification Search
CPC .................................................... A61P 31/04
See application file for complete search history.

(56) References Cited

U.S. PATENT DOCUMENTS

| | | |
|---|---|---|
| 4,182,758 A | 1/1980 | Kamiya et al. |
| 9,593,136 B2 | 3/2017 | Boshoff et al. |
| 11,098,072 B2 | 8/2021 | Dowd et al. |
| 2019/0030056 A1 | 1/2019 | Dowd et al. |

FOREIGN PATENT DOCUMENTS

| | | |
|---|---|---|
| AT | 364455 B | 10/1981 |
| WO | WO-2017127805 A1 | 7/2017 |
| WO | WO-2019005982 A1 | 1/2019 |

OTHER PUBLICATIONS

Edwards, R. L., et al., "Potent, Specific Mepicides for Treatment of Zoonotic Staphylococci," *PLoS Pathogens* 16(6):e1007806, Public Library of Science, United States (Jun. 2020).
International Search Report and Written Opinion for International Application No. PCT/US2019/037761, Commissioner for Patents, Virginia, United States, mailed on Aug. 9, 2019, 9 pages.
Jose, G. S., et al., "Structure-Activity Relationships of the MEPicides: N-Acyl and O-Linked Analogs of FR900098 as Inhibitors of Dxr From Mycobacterium Tuberculosis and Yersinia Pestis," *ACS Infectious Diseases* 2(12):923-935, ACS Publications, United States (Dec. 2016).
Pubchem, "[3-[Acetyl(hydroxy)amino]propyl-(benzoyloxymethoxy)phosphoryl]oxymethyl benzoate," created Jan. 16, 2012, 8 pages, accessed on Jul. 25, 2019, accessed at [URL:https://pubchem.ncbi.nlm.nih.gov/compound/54764844].
Pubchem, "[[(E)-3-[Acetyl(hydroxy)amino]prop-1-enyl]-(2,2-dimethylpropanoyloxymethoxy) phosphoryl]oxymethyl 2,2-dimethylpropanoate," created Mar. 17, 2014, 11 pages, accessed on Jul. 25, 2019, accessed at [URL:https://pubchem.ncbi.nlm.nih.gov/compound/73212867].
Pubchem, "[(E)-3-[Acetyl(hydroxy)amino]prop-2-enoyl]phosphonic acid," created Dec. 5, 2007, 7 pages, accessed on Jul. 25, 2019, accessed at [URL: https://pubchem.ncbi.nlm.nih.gov/compound/22644543].
Smidkova, M., et al., "Amidate Prodrugs of 9-[2-(Phosphonomethoxy) Ethyl] Adenine as Inhibitors of Adenylate Cyclase Toxin from Bordetella Pertussis," *Antimicrobial Agents and Chemotherapy* 58(2):664-671, American Society for Microbiology, United States (2014).
Wang, X. and Dowd, C. S., "The Methylerythritol Phosphate Pathway: Promising Drug Targets in the Fight against Tuberculosis," *ACS Infectious Diseases* 4(3):278-290, ACS Publications, United States (Mar. 2018).
Bjorkelid, C., et al., "Structural Studies on Mycobacterium Tuberculosis DXR in Complex With the Antibiotic FR-900098," *Acta Crystallographica Section, D, Biological Crystallography* 68(Pt 2): 134-143, Wiley-Blackwell, United States (Feb. 2012).

(Continued)

*Primary Examiner* — Brian E McDowell
(74) *Attorney, Agent, or Firm* — Sterne, Kessler, Goldstein & Fox P.L.L.C.

(57) ABSTRACT

The present disclosure provides method of treating or preventing a microbial infection caused by a prokaryotic pathogen in a subject, the method comprising administering a compound of Formula (I) as set forth in the specification. In one embodiment, the prokaryotic pathogen belongs to the genus *Staphylococcus*.

5 Claims, 8 Drawing Sheets

(56) References Cited

OTHER PUBLICATIONS

Edwards, R.L., et al., "MEPicides: Potent Antimalarial Prodrugs Targeting Isoprenoid Biosynthesis," Scientific Reports 7(1):8400, Nature Publishing Group, United Kingdom (Aug. 2017).

Guggisberg, A.M., et al., "A Sugar Phosphatase Regulates the Methylerythritol Phosphate (MEP) Pathway in Malaria Parasites," Nature Communications 5:4467, Nature Publishing Group, United Kingdom (Jul. 2014).

International Search Report and Written Opinion for Application PCT/US2018/039777, mailed on Oct. 29, 2018, 9 pages, Commissioner of Patents, Alexandria, VA.

Jackson, E.R., et al., "The Effect of Chain Length and Unsaturation on Mtb Dxr Inhibition and Antitubercular Killing Activity of FR900098 Analogs," Bioorganic & Medicinal Chemistry Letters 24(2):649-653, Elsevier Science Ltd, United Kingdom (Jan. 2014).

Pubchem, Substance Record for SID 128496555, Available Date: Dec. 4, 2011 [retrieved on Aug. 7, 2018]. Retrieved from the Internet: (URL:https://pubchem.ncbi.nlm.nih.gov/substance/128496555), entire document.

Giessmann, D., et al., "Towards New Antimalarial Drugs: Synthesis of Non-Hydrolyzable Phosphate Mimics as Feed for a Predictive QSAR Study on 1-Deoxy-D-xylulose-5-phosphate Reductoisomerase Inhibitors," Chemistry & Biodiversity 5(4):643-656, Wiley Online Library, United States (Apr. 2008).

Haemers, T., et al., "Synthesis of beta- and gamma-oxa isosteres of fosmidomycin and FR900098 as antimalarial candidates," Bioorg Med Chem 16(6):3361-3371, Elsevier Ltd., United Kingdom (Mar. 2008).

Kuntz, L., et al., "Isoprenoid biosynthesis as a target for antibacterial and antiparasitic drugs: phosphonohydroxamic acids as inhibitors of deoxyxylulose phosphate reducto-isomerase," Biochem J 386(Pt 1):127-135, Portland Press Ltd., United Kingdom (Feb. 2005).

Munier, M., et al., "Synthesis and biological evaluation of phosphate isosters of fosmidomycin and analogs as inhibitors of *Escherichia coli* and Mycobacterium smegmatis 1-deoxyxylulose 5-phosphate reductoisomerases," Bioorg Med Chem 25(2):684-689, Elsevier Ltd., United Kingdom (Jan. 2017).

Ponaire, S., et al., "Growth inhibition of Mycobacterium smegmatis by prodrugs of deoxyxylulose phosphate reducto-isomerase inhibitors, promising anti-mycobacterial agents," Eur J Med Chem 51:277-285 Elsevier Masson S.R.L., France (May 2012).

Zingle, C., et al., "Isoprenoid biosynthesis via the methylerythritol phosphate pathway: structural variations around phosphonate anchor and spacer of fosmidomycin, a potent inhibitor of deoxyxylulose phosphate reductoisomerase," J Org Chem 75(10):3203-3207, American Chemical Society, United States (May 2010).

ANTIBIOTICS FOR VETERINARY STAPHYLOCOCCAL INFECTIONS

GOVERNMENT LICENSE RIGHTS

This invention was made with government support under Grant No. R21 AI123808 and R01 AI123433 awarded by the National Institutes of Health. The U.S. government has certain rights in the invention.

BACKGROUND

1. Technical Field

The field of the present disclosure relates to compounds, methods, and pharmaceutical compositions for treating or preventing infection caused by Staphylococcal species.

2. Discussion of Related Art

Antimicrobial resistance is the ability of a microbe to resist the effects of an antibiotic. This means that microbes are not killed by the antibiotic and can continue to grow. There is a growing burden of antimicrobial resistance in animals. The key bacterial pathogens in infections, e.g., skin and soft tissue infections, in animals, are members of the *Staphylococcus intermedius* group. In particular, animals are increasingly infected by methicillin-resistant *Staphylococcus pseudintermedius* (MRSP) and methicillin-resistant *Staphylococcus schleiferi* (MRSS). New therapies are urgently needed.

Fosmidomycin (Scheme 1, 1a), isolated from *Streptomyces lavendulae*, is a potent inhibitor of *P. falciparum* DXR ($IC_{50}$=0.034 µM). FR900098 (Scheme 1, 1b), the N-acetyl analog of fosmidomycin isolated from *Streptomyces rubellomurinus*, is roughly equipotent to fosmidomycin (*P. falciparum* DXR $IC_{50}$=0.024 µM). While these two natural products have submicromolar inhibition of *P. falciparum* growth ($IC_{50}$=0.09-0.35 µM), their use as a single drug therapy is limited by low bioavailability, short serum half-life, and malaria recrudescence.

Scheme 1

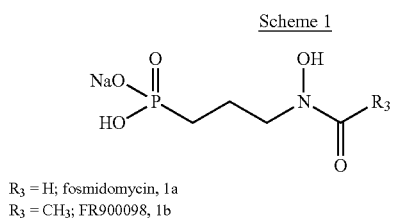

R₃ = H; fosmidomycin, 1a
R₃ = CH₃; FR900098, 1b

WO 2019/005982 and US 2019/0030056 disclose α,β-unsaturated analogs of fosmidomycin that inhibit microbial infections caused by eukaryotic pathogens.

BRIEF SUMMARY OF THE INVENTION

Applicant has discovered that compounds of the present disclosure are not active against *S. aureus* pathogens but are active against other *Staphylococcus* pathogens such as *S. schleiferi*, *S. pseudintermedius*, and/or *S. chromogenes*. This selectivity among prokaryotic *Staphylococcus* pathogens was unexpected.

In one aspect, the present disclosure provides a compound of Formula (I):

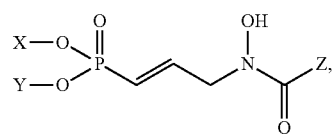

wherein:
X is selected from the group consisting of Na, H, and CH($R_1$)OC(=O)$R_2$;
Y is selected from the group consisting of Na, H, and CH($R_1$)OC(=O)$R_2$;
Z is selected from the group consisting of hydrogen, $C_1$-$C_6$ alkyl, optionally substituted aryl, and aralkyl;
each $R_1$ is independently selected from the group consisting of a hydrogen, $C_1$-$C_6$ alkyl, and optionally substituted aryl;
each $R_2$ is independently selected from the group consisting of an optionally substituted $C_1$-$C_6$ alkyl, optionally substituted $C_2$-$C_6$ alkenyl, optionally substituted $C_3$-$C_6$ cycloalkyl, and optionally substituted aryl, or a pharmaceutically acceptable salt thereof.

In another aspect, the present disclosure provides a composition comprising:
(i) a compound of Formula (I), or a pharmaceutically acceptable salt thereof; and
(ii) a pharmaceutically acceptable excipient.

In another aspect, the present disclosure provides a method for treating or preventing a microbial infection in a subject in need thereof, the method comprising administering to the subject an effective amount of a compound of Formula (I), or a pharmaceutically acceptable salt thereof.

DETAILED DESCRIPTION OF THE INVENTION

Figure 1:
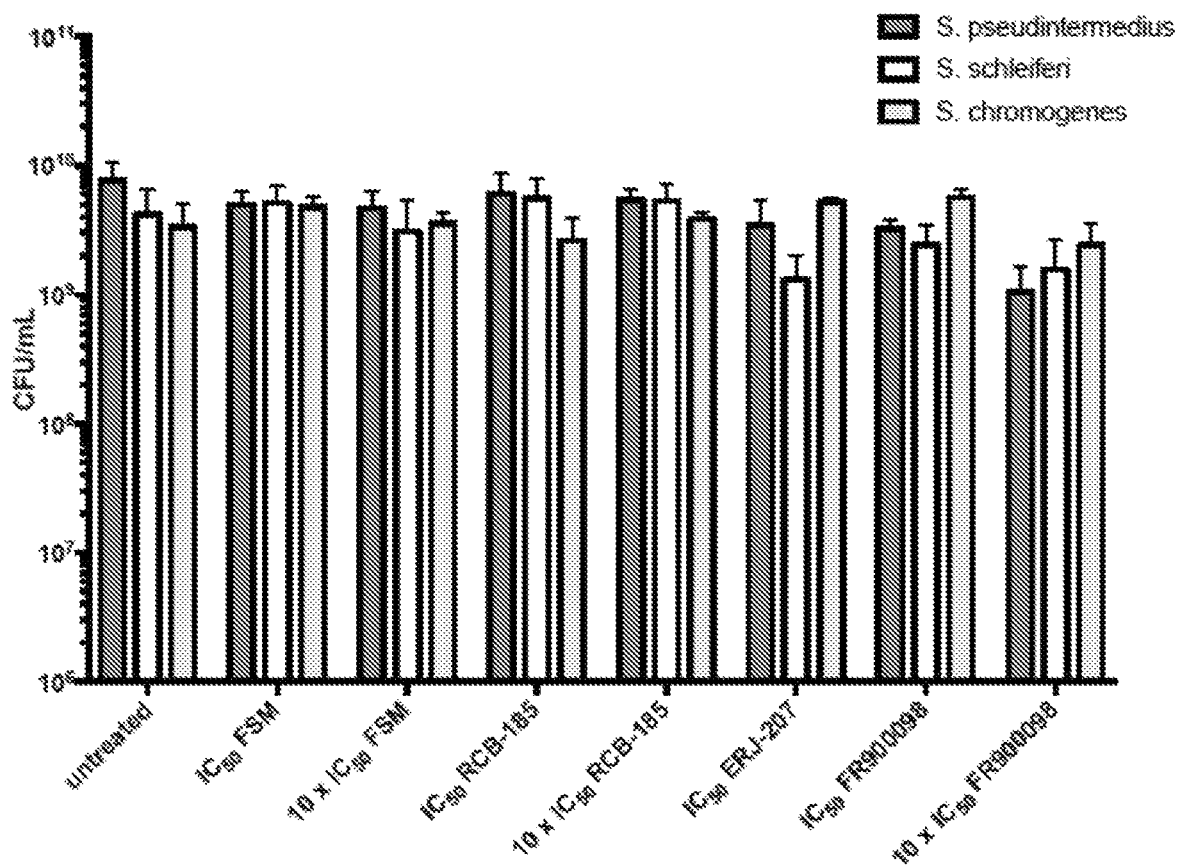
FIG. 1 is a bar graph showing that fosmidomycin (FSM), FR900098, and representative compounds of Formula (I) are bacteriostatic in *S. schleferi*, *S. pseudintermedius*, and *S. chromogenes*.
Figure 2:
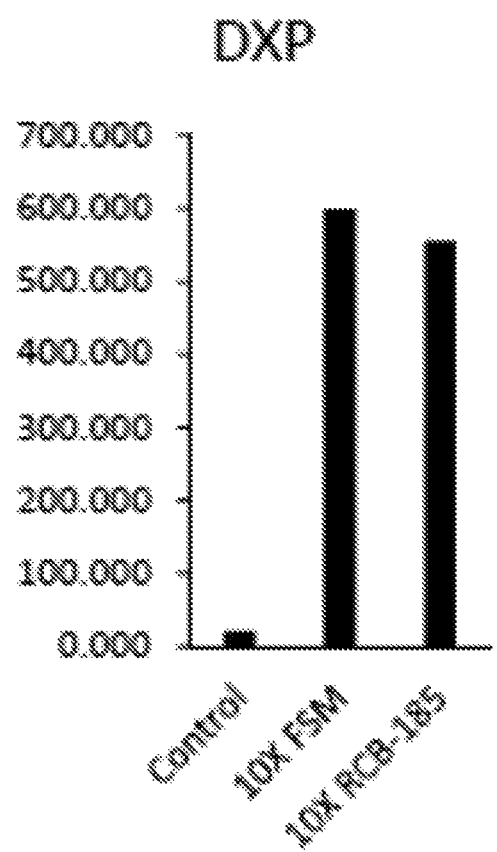
FIG. 2 is a bar graph showing DXP metabolite analysis of *S. pseudintermedius* treated with FSM and RCB-185.
Figure 3:
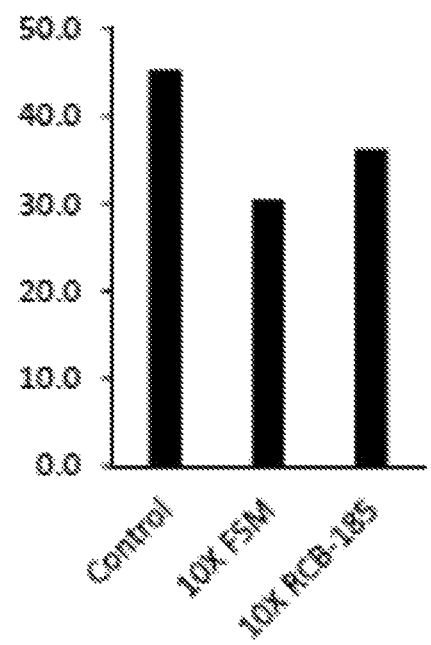
FIG. 3 is a bar graph showing MEP metabolite analysis of *S. pseudintermedius* treated with FSM and RCB-185.
Figure 4:
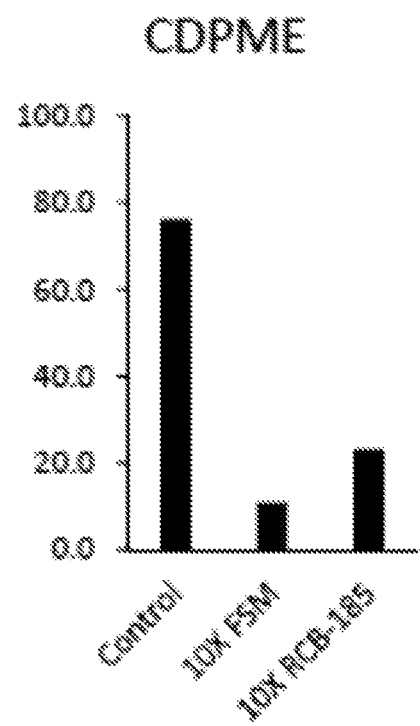
FIG. 4 is a bar graph showing CDPME metabolite analysis of *S. pseudintermedius* treated with FSM and RCB-185.
Figure 5:
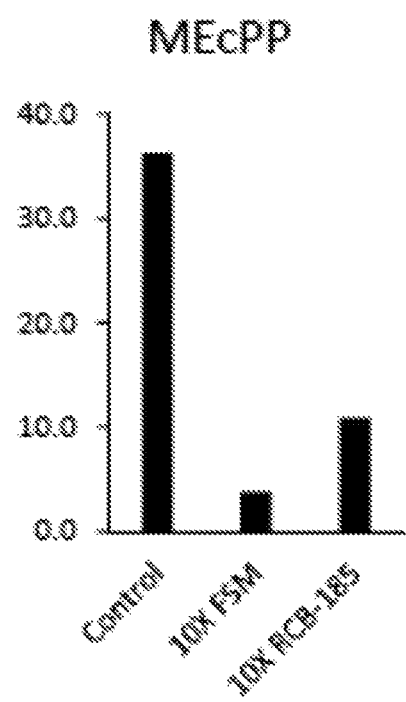
FIG. 5 is a bar graph showing MEcPP metabolite analysis of *S. pseudintermedius* treated with FSM and RCB-185.
Figure 6:
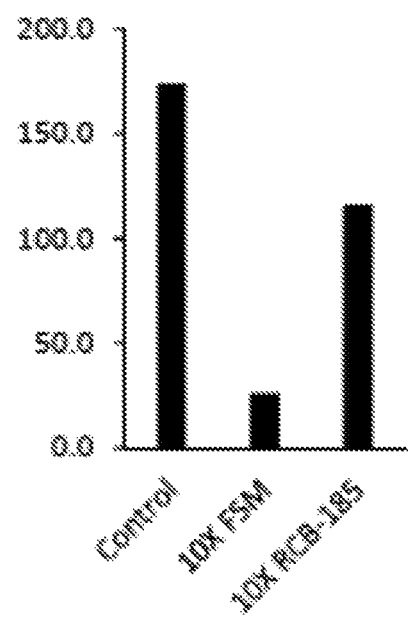
FIG. 6 is a bar graph showing HDMAPP metabolite analysis of *S. pseudintermedius* treated with FSM and RCB-185.
Figure 7:
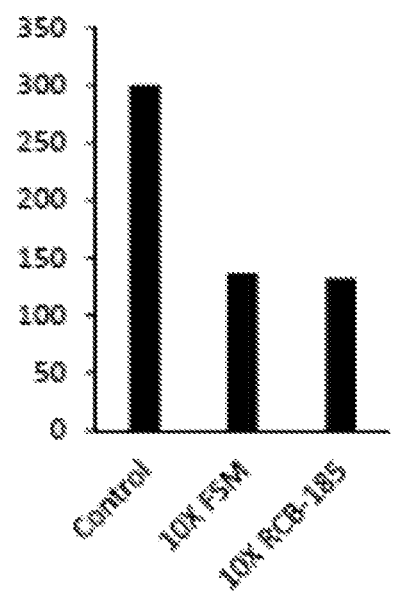
FIG. 7 is a bar graph showing IPP/DMAPP metabolite analysis of *S. pseudintermedius* treated with FSM and RCB-185.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited in this specification, including the Examples sections, are incorporated by reference as if each had been individually incorporated.

In one embodiment, the present disclosure provides a compound of Formula (I):

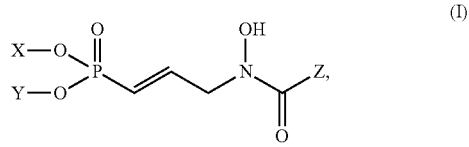

wherein:
- X is selected from the group consisting of Na, hydrogen, and $CH(R_1)OC(=O)R_2$;
- Y is selected from the group consisting of Na, hydrogen, and $CH(R_1)OC(=O)R_2$;
- Z is selected from the group consisting of hydrogen, $C_1$-$C_6$ alkyl, optionally substituted aryl, and aralkyl;
- each $R_1$ is independently selected from the group consisting of a hydrogen, $C_1$-$C_6$ alkyl, and optionally substituted aryl;
- each $R_2$ is independently selected from the group consisting of an optionally substituted $C_1$-$C_6$ alkyl, optionally substituted $C_2$-$C_6$ alkenyl, optionally substituted $C_3$-$C_6$ cycloalkyl, and optionally substituted aryl, or a pharmaceutically acceptable salt thereof.

In another embodiment, the present disclosure provides a compound of Formula (I), wherein X is selected from the group consisting of Na, hydrogen, $CH_2OC(=O)C(CH_3)_3$, and $CH_2OC(=O)Ph$, or a pharmaceutically acceptable salt thereof.

In another embodiment, the present disclosure provides a compound of Formula (I), wherein Y is selected from the group consisting of Na, hydrogen, $CH_2OC(=O)C(CH_3)_3$, and $CH_2OC(=O)Ph$, or a pharmaceutically acceptable salt thereof.

In another embodiment, the present disclosure provides a compound of Formula (I), wherein Z is selected from the group consisting of hydrogen, methyl, phenyl, and $—(CH_2)_3$Ph, or a pharmaceutically acceptable salt thereof.

In another embodiment, the present disclosure provides a compound of Formula (I) selected from any one or more of the compounds of Table 1, or a pharmaceutically acceptable salt thereof.

TABLE 1

| Formula | Structure | ID |
|---|---|---|
| II | (structure) | RCB-185 |
| III | (structure) | ERJ-207 |
| V | (structure) | JXW-572 |
| VI | (structure) | JXW-573 |
| VII | (structure) | KMH-102 |

TABLE 1-continued

| Formula | Structure | ID |
|---|---|---|
| VIII | 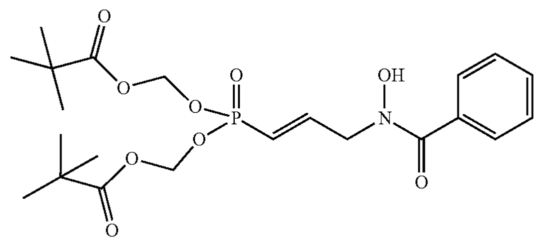 [SMILES: CC(C)(C)C(=O)OCOP(=O)(/C=C/CN(O)C(=O)c1ccccc1)OCOC(=O)C(C)(C)C] | JXW-189 |
| IX | 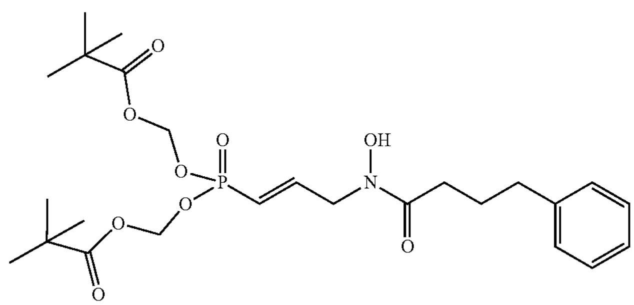 [SMILES: CC(C)(C)C(=O)OCOP(=O)(/C=C/CN(O)C(=O)CCCc1ccccc1)OCOC(=O)C(C)(C)C] | JXW-168 |
| X | 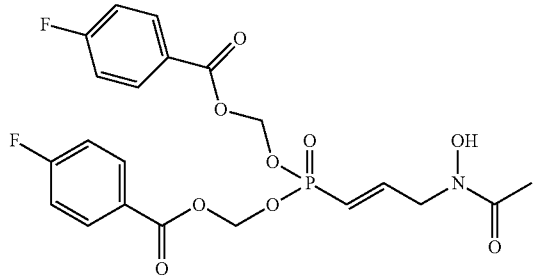 [SMILES: CC(=O)N(O)C/C=C/P(=O)(OCOC(=O)c1ccc(F)cc1)OCOC(=O)c1ccc(F)cc1] | CSD-101 |
| XI | 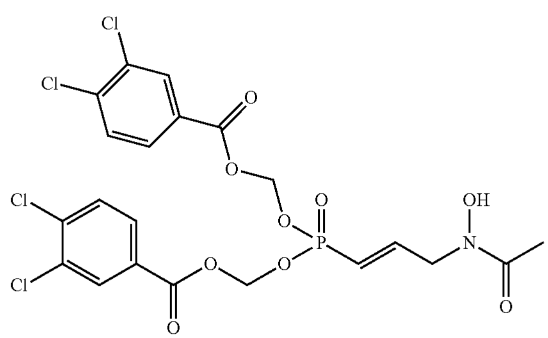 [SMILES: CC(=O)N(O)C/C=C/P(=O)(OCOC(=O)c1ccc(Cl)c(Cl)c1)OCOC(=O)c1ccc(Cl)c(Cl)c1] | CSD-102 |
| XII | 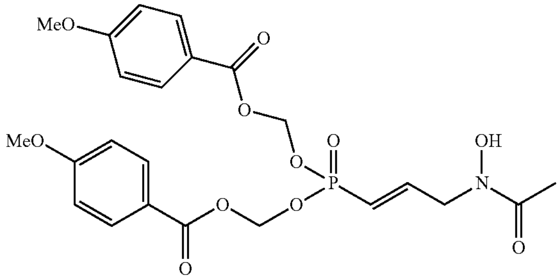 [SMILES: COc1ccc(C(=O)OCOP(=O)(/C=C/CN(O)C(C)=O)OCOC(=O)c2ccc(OC)cc2)cc1] | CSD-103 |

TABLE 1-continued

| Formula | Structure | ID |
|---|---|---|
| XIII | 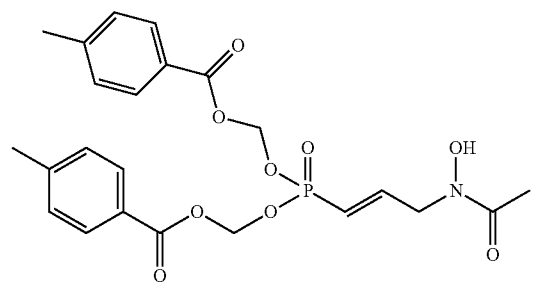 [SMILES: CC(=O)N(O)C/C=C/P(=O)(OCOC(=O)c1ccc(C)cc1)OCOC(=O)c1ccc(C)cc1] | CSD-104 |
| XIV | 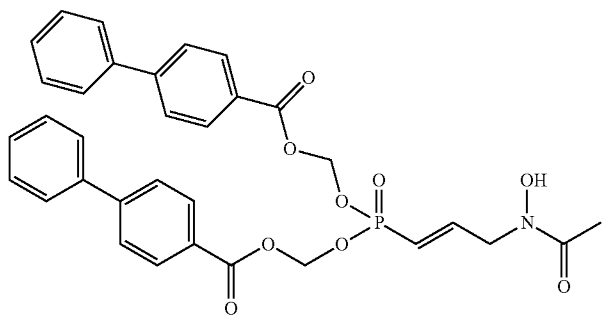 [SMILES: CC(=O)N(O)C/C=C/P(=O)(OCOC(=O)c1ccc(-c2ccccc2)cc1)OCOC(=O)c1ccc(-c2ccccc2)cc1] | CSD-105 |
| XV | 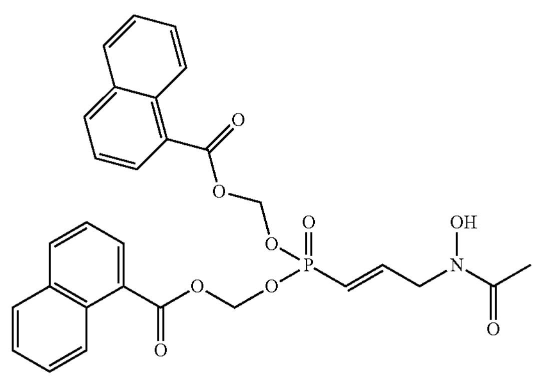 [SMILES: CC(=O)N(O)C/C=C/P(=O)(OCOC(=O)c1cccc2ccccc12)OCOC(=O)c1cccc2ccccc12] | CSD-106 |
| XVI | 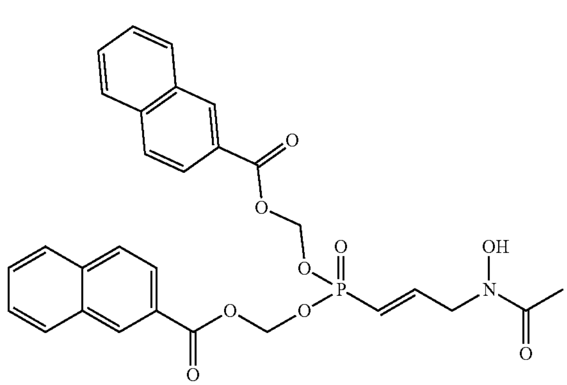 [SMILES: CC(=O)N(O)C/C=C/P(=O)(OCOC(=O)c1ccc2ccccc2c1)OCOC(=O)c1ccc2ccccc2c1] | CSD-107 |

TABLE 1-continued

| Formula | Structure | ID |
|---|---|---|
| XVII | 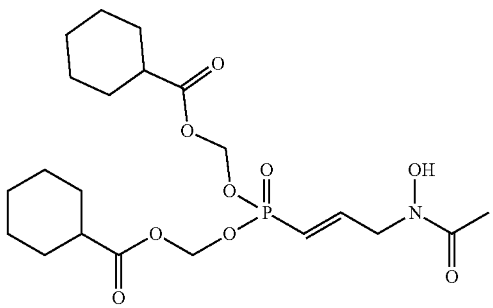 [SMILES: CC(=O)N(O)C/C=C/P(=O)(OCOC(=O)C1CCCCC1)OCOC(=O)C1CCCCC1] | CSD-108 |

In another embodiment, the present disclosure provides a compound having Formula (XVIII):

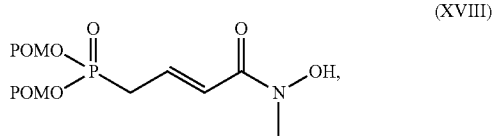
(XVIII)

or a pharmaceutically acceptable salt thereof.

In another embodiment, the present disclosure provides a composition comprising: (i) a compound of Formula (I), or a pharmaceutically acceptable salt thereof; and (ii) a pharmaceutically acceptable excipient.

In another embodiment, the present disclosure provides a composition comprising: (i) a compound of Formula (I), or a pharmaceutically acceptable salt thereof, wherein X is selected from the group consisting of Na, hydrogen, $CH_2OC(=O)C(CH_3)_3$, and $CH_2OC(=O)Ph$; and (ii) a pharmaceutically acceptable excipient.

In another embodiment, the present disclosure provides a composition comprising: (i) a compound of Formula (I), or a pharmaceutically acceptable salt thereof, wherein Y is selected from the group consisting of Na, hydrogen, $CH_2OC(=O)C(CH_3)_3$, and $CH_2OC(=O)Ph$; and (ii) a pharmaceutically acceptable excipient.

In another embodiment, the present disclosure provides a composition comprising: (i) a compound of Formula (I), or a pharmaceutically acceptable salt thereof, wherein Z is selected from the group consisting of hydrogen, methyl, phenyl, and $—(CH_2)_3Ph$; and (ii) a pharmaceutically acceptable excipient.

In another embodiment, the present disclosure provides a composition comprising: (i) a compound of Formula (I) selected from any one or more of the compounds of Table 1, or a pharmaceutically acceptable salt thereof; and (ii) a pharmaceutically acceptable excipient.

In another embodiment, the present disclosure provides a method for treating or preventing a microbial infection in a subject in need thereof, the method comprising administering to the subject an effective amount of a compound of Formula (I), or a pharmaceutically acceptable salt thereof.

In another embodiment, the present disclosure provides a method for treating or preventing a microbial infection in a subject in need thereof, the method comprising administering to the subject an effective amount of a compound of Formula (I), or a pharmaceutically acceptable salt thereof, wherein X is selected from the group consisting of Na, hydrogen, $CH_2OC(=O)C(CH_3)_3$, and $CH_2OC(=O)Ph$.

In another embodiment, the present disclosure provides a method for treating or preventing a microbial infection in a subject in need thereof, the method comprising administering to the subject an effective amount of a compound of Formula (I), or a pharmaceutically acceptable salt thereof, wherein Y is selected from the group consisting of Na, hydrogen, $CH_2OC(=O)C(CH_3)_3$, and $CH_2OC(=O)Ph$.

In another embodiment, the present disclosure provides a method for treating or preventing a microbial infection in a subject in need thereof, the method comprising administering to the subject an effective amount of a compound of Formula (I), or a pharmaceutically acceptable salt thereof, wherein Z is selected from the group consisting of hydrogen, methyl, phenyl and $—(CH_2)_3Ph$.

In another embodiment, the present disclosure provides a method for treating or preventing a microbial infection in a subject in need thereof, the method comprising administering to the subject an effective amount of a compound of Formula (I) selected from any one or more of the compounds of Table 1, or a pharmaceutically acceptable salt thereof.

In another embodiment, the present disclosure provides a method for treating or preventing a microbial infection in a subject in need thereof, the method comprising administering to the subject an effective amount of fosmidomycin or FR-900098, or a pharmaceutically acceptable salt thereof.

In another embodiment, the present disclosure provides a method for treating or preventing a microbial infection in a subject in need thereof, the method comprising administering to the subject an effective amount of a compound of Formula (XVIII), or a pharmaceutically acceptable salt thereof.

In another embodiment, the microbial infection is caused by a prokaryotic pathogen.

In another embodiment, the compound of Formula (I) inhibits a function of an enzyme in a methylerythritol phosphate (MEP) pathway.

In another embodiment, the prokaryotic pathogen belongs to the genus *Staphylococcus*.

In another embodiment, the prokaryotic pathogen is *S. schleferi*, *S. pseudintermedius*, or *S. chromogenes*.

In another embodiment, the microbial infection is a Staphylococcal infection.

In another embodiment, the compound of Formula (I) inhibits the function of the enzyme by binding to the enzyme.

In another embodiment, the enzyme is Dxr.

In another embodiment, the compound of Formula (I) is administered in combination with an effective amount of an additional compound or composition, wherein the additional compound or composition treats or prevents the microbial infection or a secondary infection or a secondary symptom.

In another embodiment, the present disclosure provides a method for inhibiting the growth of a prokaryotic pathogen, the method comprising contacting the prokaryotic pathogen with an effective amount of a compound of Formula (I), or a pharmaceutically acceptable salt thereof.

In another embodiment, the present disclosure provides a method for inhibiting the growth of a prokaryotic pathogen, the method comprising contacting the prokaryotic pathogen with effective amount of a compound of Formula (I), or a pharmaceutically acceptable salt thereof, wherein X is selected from the group consisting of Na, hydrogen, $CH_2OC(=O)C(CH_3)_3$, and $CH_2OC(=O)Ph$.

In another embodiment, the present disclosure provides a method for inhibiting the growth of a prokaryotic pathogen, the method comprising contacting the prokaryotic pathogen with an effective amount of a compound of Formula (I), or a pharmaceutically acceptable salt thereof, wherein Y is selected from the group consisting of Na, hydrogen, $CH_2OC(=O)C(CH_3)_3$, and $CH_2OC(=O)Ph$.

In another embodiment, the present disclosure provides a method for inhibiting the growth of a prokaryotic pathogen, the method comprising contacting the prokaryotic pathogen with an effective amount of a compound of Formula (I), or a pharmaceutically acceptable salt thereof, wherein Z is selected from the group consisting of hydrogen, methyl, phenyl and $—(CH_2)_3Ph$.

In another embodiment, the present disclosure provides a method for inhibiting the growth of a prokaryotic pathogen, the method comprising contacting the prokaryotic pathogen with an effective amount of a compound of Formula (I) selected from any one or more of the compounds of Table 1, or a pharmaceutically acceptable salt thereof.

In another embodiment, the present disclosure provides a method for inhibiting the growth of a prokaryotic pathogen, the method comprising contacting the prokaryotic pathogen with an effective amount of fosmidomycin or FR-900098, or a pharmaceutically acceptable salt thereof.

In another embodiment, the present disclosure provides a method for inhibiting the growth of a prokaryotic pathogen, the method comprising contacting the prokaryotic pathogen with an effective amount of a compound of Formula (XVIII), or a pharmaceutically acceptable salt thereof.

In another embodiment, the prokaryotic pathogen belongs to the genus *Staphylococcus*.

In another embodiment, the present disclosure relates to a method for treating or preventing a microbial infection in a subject in need thereof comprising administering to the subject an effective amount of a composition or formulation comprising a small molecule having the structure of Formula (I):

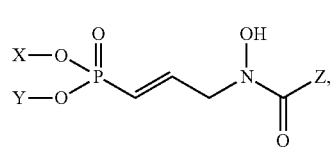

or pharmaceutically acceptable salts and prodrugs thereof, where X is selected from the group consisting of Na, H, $CH(R_1)OC(=O)C(CH_3)_3$, $CH_2OC(=O)R_2$ and POM, where Y is selected from the group consisting of Na, H, and POM, where Z is $CH_3$, H, unsubstituted Phenyl or substituted Phenyl, where $R_1$ is selected from the group consisting of a methyl group, an ethyl group, a propyl group and an aryl group, where $R_2$ is selected from the group consisting of an unsubstituted aryl group, an unsubstituted alkyl group, an unsubstituted alkenyl group, a substituted aryl group, a substituted alkyl group, and a substituted alkenyl group, where POM is $CH_2OC(=O)C(CH_3)_3$, where the microbial infection is caused by a prokaryotic pathogen, and where the small molecule inhibits a function of an enzyme in a methylerythritol phosphate (MEP) pathway.

Some embodiments of the present disclosure relate to the method above, where the prokaryotic pathogen belongs to the genus *Staphylococcus*.

Some embodiments of the present disclosure relate to the method above, where the small molecule inhibits the function of the enzyme by binding to the enzyme.

Some embodiments of the present disclosure relate to the method above, where the enzyme is Dxr.

Some embodiments of the present disclosure relate to the method above, where the effective amount is between 0.1 mg/kg of body weight of the subject to 300 mg/kg of body weight of the subject.

Some embodiments of the present disclosure relate to the method above, where the composition or formulation is administered to the subject as a single dose or as multiple doses over the course of a single day or multiple days.

Some embodiments of the present disclosure relate to the method above, where the composition or formulation is administered to the subject for at least 1 day.

Some embodiments of the present disclosure relate to the method above, further comprising administering to the subject an additional composition or formulation, wherein the additional composition or formulation treats the microbial infection or a secondary infection or a secondary symptom.

Some embodiments of the present disclosure relate to the method above, where the small molecule has the structure of Formula (II):

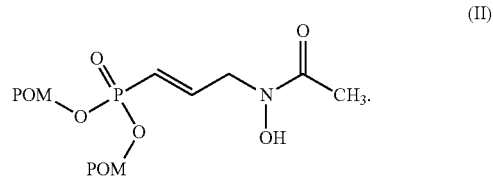

Some embodiments of the present disclosure relate to the method above, where the small molecule has the structure of Formula (III):

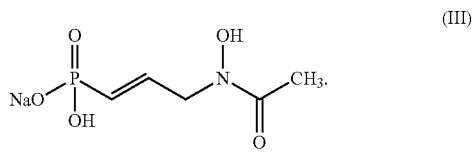

Some embodiments of the present disclosure relate to the method above, where the small molecule has the structure of Formula (IV):

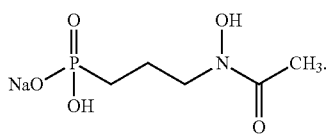
(IV)

Some embodiments of the present disclosure relate to the method above, where the small molecule has the structure of Formula (V):

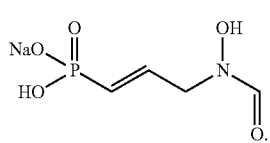
(V)

Some embodiments of the present disclosure relate to the method above, where the small molecule has the structure of Formula (VI):

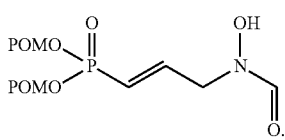
(VI)

In another embodiment, the present disclosure relates to a method for inhibiting growth of a prokaryotic pathogen comprising contacting the prokaryotic pathogen with effective amount of a small molecule having the structure of Formula (I):

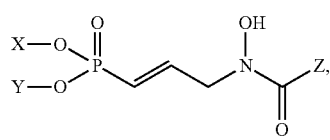
(I)

or pharmaceutically acceptable salts and prodrugs thereof, where X is selected from the group consisting of Na, H, $CH(R_1)OC(=O)C(CH_3)_3$, $CH_2OC(=O)R_2$ and POM, where Y is selected from the group consisting of Na, H, and POM, where Z is $CH_3$, H, unsubstituted Phenyl or substituted Phenyl, where $R_1$ is selected from the group consisting of a methyl group, an ethyl group, a propyl group and an aryl group, where $R_2$ is selected from the group consisting of an unsubstituted aryl group, an unsubstituted alkyl group, an unsubstituted alkenyl group, a substituted aryl group, a substituted alkyl group, and a substituted alkenyl group, where POM is $CH_2OC(=O)C(CH_3)_3$, and where the small molecule inhibits a function of an enzyme in a methylerythritol phosphate (MEP) pathway.

Some embodiments of the present disclosure relate to the method above, where the prokaryotic pathogen belongs to the genus *Staphylococcus*.

Some embodiments of the present disclosure relate to the method above, where the small molecule inhibits the function of the enzyme by binding to the enzyme.

Some embodiments of the present disclosure relate to the method above, where the enzyme is Dxr.

Some embodiments of the present disclosure relate to the method above, further comprising contacting the prokaryotic pathogen with an additional composition or formulation, wherein the additional composition inhibits a biological process of the prokaryotic pathogen.

Some embodiments of the present disclosure relate to the method above, where the small molecule has the structure of Formula (II):

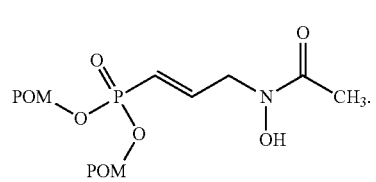
(II)

Some embodiments of the present disclosure relate to the method above, where the small molecule has the structure of Formula (III):

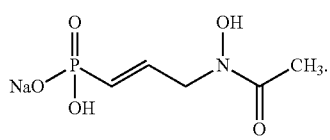
(III)

Some embodiments of the present disclosure relate to the method above, where the small molecule has the structure of Formula (IV):

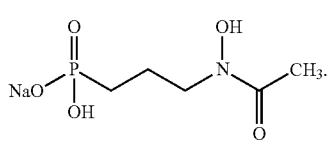
(IV)

Some embodiments of the present disclosure relate to the method above, where the small molecule has the structure of Formula (V):

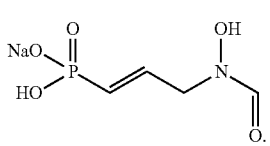
(V)

Some embodiments of the present disclosure relate to the method above, where the small molecule has the structure of Formula (VI):

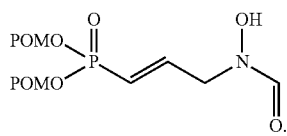

In another embodiment, the present disclosure relates a pharmaceutical composition comprising a small molecule having the structure of Formula (I):

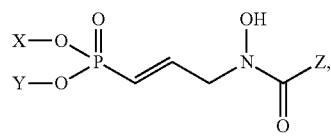

or pharmaceutically acceptable salts and prodrugs thereof; and a pharmaceutically acceptable excipient, where X is selected from the group consisting of Na, H, $CH(R_1)OC(=O)C(CH_3)_3$, $CH_2OC(=O)R_2$ and POM, where Y is selected from the group consisting of Na, H, and POM, where Z is $CH_3$, H, unsubstituted Phenyl or substituted Phenyl, where $R_1$ is selected from the group consisting of a methyl group, an ethyl group, a propyl group and an aryl group, where $R_2$ is selected from the group consisting of an unsubstituted aryl group, an unsubstituted alkyl group, an unsubstituted alkenyl group, a substituted aryl group, a substituted alkyl group, and a substituted alkenyl group, and where POM is $CH_2OC(=O)C(CH_3)_3$.

Some embodiments of the present disclosure relate to the pharmaceutical composition above, where the small molecule has the structure of Formula (II):

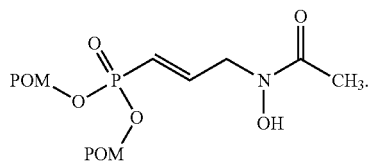

Some embodiments of the present disclosure relate to the pharmaceutical composition above, where the small molecule has the structure of Formula (III):

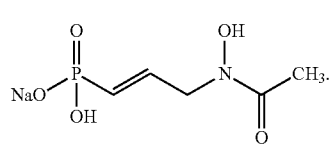

Some embodiments of the present disclosure relate to the pharmaceutical composition above, where the small molecule has the structure of Formula (IV):

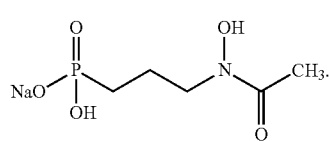

Some embodiments of the present disclosure relate to the pharmaceutical composition above, where the small molecule has the structure of Formula (V):

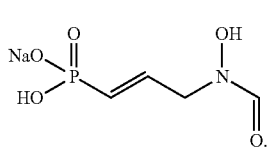

Some embodiments of the current invention relate to the pharmaceutical composition above, where the small molecule has the structure of Formula (VI):

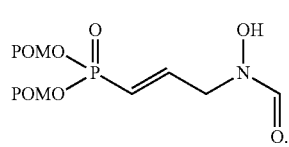

The disclosure also provides the following particular embodiments.

Embodiment I. A method for treating or preventing a microbial infection in a subject in need thereof comprising administering to the subject an effective amount of a composition or formulation comprising a small molecule having the structure of Formula (I)

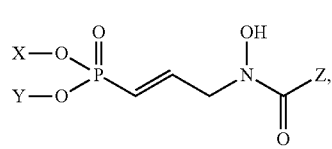

or pharmaceutically acceptable salts and prodrugs thereof,
  wherein X is selected from the group consisting of Na, H, $CH(R_1)OC(=O)C(CH_3)_3$, $CH_2OC(=O)R_2$ and POM,
  wherein Y is selected from the group consisting of Na, H, and POM,
  wherein Z is $CH_3$, H, unsubstituted Phenyl or substituted Phenyl,
  wherein $R_1$ is selected from the group consisting of a methyl group, an ethyl group, a propyl group and an aryl group,
  wherein $R_2$ is selected from the group consisting of an unsubstituted aryl group, an unsubstituted alkyl group, an unsubstituted alkenyl group, a substituted aryl group, a substituted alkyl group, and a substituted alkenyl group,
  wherein POM is $CH_2OC(=O)C(CH_3)_3$,
  wherein the microbial infection is caused by a prokaryotic pathogen, and wherein the small molecule inhibits a function of an enzyme in a methylerythritol phosphate (MEP) pathway.

Embodiment 2. The method of Embodiment 1, wherein the prokaryotic pathogen belongs to the genus *Staphylococcus*.

Embodiment 3. The method of Embodiment 1, wherein the small molecule inhibits the function of the enzyme by binding to the enzyme.

Embodiment 4. The method of Embodiment 1, wherein the enzyme is Dxr.

Embodiment 5. The method of Embodiment 1, wherein the effective amount is between 0.1 mg/kg of body weight of the subject to 300 mg/kg of body weight of the subject.

Embodiment 6. The method of Embodiment 1, wherein the composition or formulation is administered to the subject as a single dose or as multiple doses over the course of a single day or multiple days.

Embodiment 7. The method of Embodiment 1, wherein the composition or formulation is administered to the subject for at least 1 day.

Embodiment 8. The method of Embodiment 1, further comprising administering to the subject an additional composition or formulation, wherein the additional composition or formulation treats the microbial infection or a secondary infection or a secondary symptom.

Embodiment 9. The method of Embodiment 1, wherein the small molecule has the structure of Formula (II):

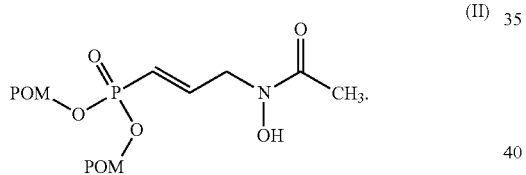

(II)

Embodiment 10. The method of Embodiment 1, wherein the small molecule has the structure of Formula (III):

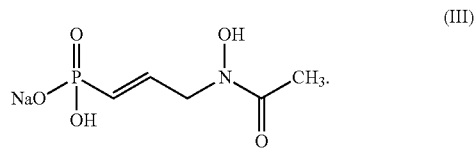

(III)

Embodiment 11. The method of Embodiment 1, wherein the small molecule has the structure of Formula (IV):

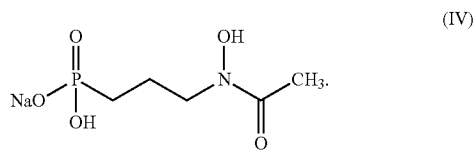

(IV)

Embodiment 12. The method of Embodiment 1, wherein the small molecule has the structure of Formula (V):

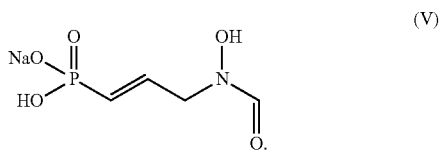

(V)

Embodiment 13. The method of Embodiment 1, wherein the small molecule has the structure of Formula (VI):

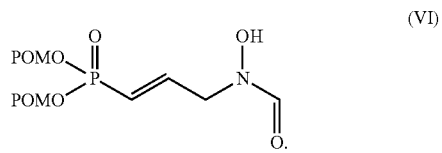

(VI)

Embodiment 14. A method for inhibiting growth of a prokaryotic pathogen comprising contacting the prokaryotic pathogen with effective amount of a small molecule having the structure of Formula (I):

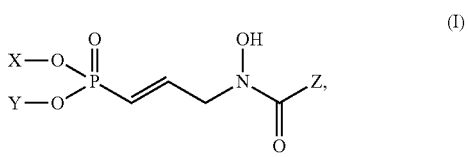

(I)

or pharmaceutically acceptable salts and prodrugs thereof,
wherein X is selected from the group consisting of Na, H, $CH(R_1)OC(=O)C(CH_3)_3$, $CH_2OC(=O)R_2$ and POM,
wherein Y is selected from the group consisting of Na, H, and POM,
wherein Z is $CH_3$, H, unsubstituted Phenyl or substituted Phenyl,
wherein $R_1$ is selected from the group consisting of a methyl group, an ethyl group, a propyl group and an aryl group,
wherein $R_2$ is selected from the group consisting of an unsubstituted aryl group, an unsubstituted alkyl group, an unsubstituted alkenyl group, a substituted aryl group, a substituted alkyl group, and a substituted alkenyl group,
wherein POM is $CH_2OC(=O)C(CH_3)_3$,
wherein the small molecule inhibits a function of an enzyme in a methylerythritol phosphate (MEP) pathway.

Embodiment 15. The method of Embodiment 14, wherein the prokaryotic pathogen belongs to the genus *Staphylococcus*.

Embodiment 16. The method of Embodiment 14, wherein the small molecule inhibits the function of the enzyme by binding to the enzyme.

Embodiment 17. The method Embodiment claim 14, wherein the enzyme is Dxr.

Embodiment 18. The method of Embodiment 14, further comprising contacting the prokaryotic pathogen with an additional composition or formulation, wherein the additional composition inhibits a biological process of the prokaryotic pathogen.

Embodiment 19. The method of Embodiment 14, wherein the small molecule has the structure of Formula (II):

(II)

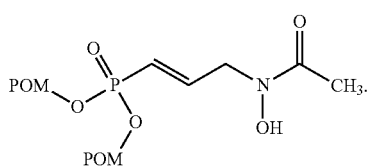

Embodiment 20. The method of claim Embodiment 14, wherein the small molecule has the structure of Formula (III):

(III)

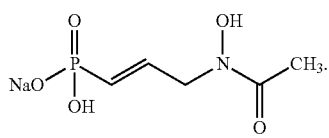

Embodiment 21. The method of Embodiment 14, wherein the small molecule has the structure of Formula (IV):

(IV)

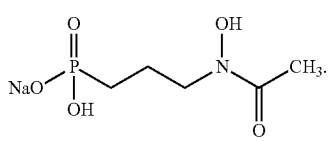

Embodiment 22. The method of Embodiment 14, wherein the small molecule has the structure of Formula (V):

(V)

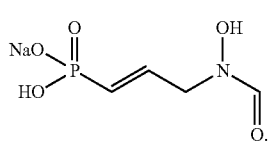

Embodiment 23. The method of Embodiment 14, wherein the small molecule has the structure of Formula (VI):

(VI)

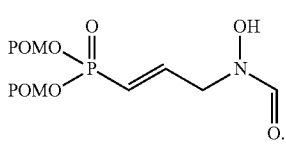

Embodiment 24. A pharmaceutical composition comprising a small molecule having the structure of Formula (I):

(I)

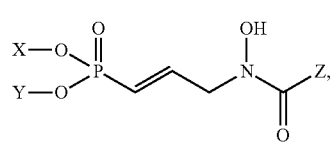

or pharmaceutically acceptable salts and prodrugs thereof; and a pharmaceutically acceptable excipient, wherein X is selected from the group consisting of Na, H, $CH(R_1)OC(=O)C(CH_3)_3$, $CH_2OC(=O)R_2$ and POM, wherein Y is selected from the group consisting of Na, H, and POM, wherein Z is $CH_3$, H, unsubstituted Phenyl or substituted Phenyl, wherein $R_1$ is selected from the group consisting of a methyl group, an ethyl group, a propyl group and an aryl group, wherein $R_2$ is selected from the group consisting of an unsubstituted aryl group, an unsubstituted alkyl group, an unsubstituted alkenyl group, a substituted aryl group, a substituted alkyl group, and a substituted alkenyl group, and wherein POM is $CH_2OC(=O)C(CH_3)_3$.

Embodiment 25. The pharmaceutical composition of Embodiment 24, wherein the small molecule has the structure of Formula (II):

(II)

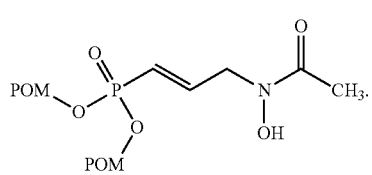

Embodiment 26. The pharmaceutical composition of Embodiment 24, wherein the small molecule has the structure of Formula (III):

(III)

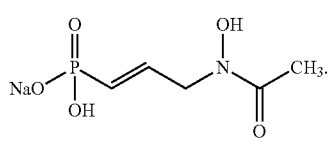

Embodiment 27. The pharmaceutical composition of Embodiment 24, wherein the small molecule has the structure of Formula (IV):

(IV)

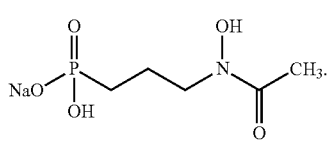

Embodiment 28. The pharmaceutical composition of Embodiment 24, wherein the small molecule has the structure of Formula (V):

(V)

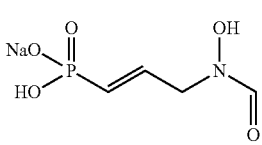

Embodiment 29. The pharmaceutical composition of Embodiment 24, wherein the small molecule has the structure of Formula (VI):

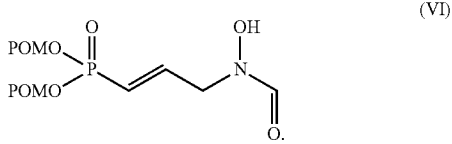

(VI)

Definitions

As used throughout the term "subject" refers to a mammal. In some embodiments, the mammal is human. In some embodiments, the mammal is an animal. In some embodiments, the animal is a companion animal/household pet. In some embodiments, the animal is livestock or other large farm animal. In some embodiments, the animal is a cow, sheep, pig, horse, dog or cat.

The term "in need thereof" refers to a subject infected with a microbial pathogen or at risk of becoming infected by the microbial pathogen. In some embodiments, the pathogen is a prokaryotic pathogen. In some embodiments, the pathogen belongs to the genus *Staphylococcus*.

As used throughout, the phrase an "effective amount" of a compound of this disclosure is measured by the therapeutic effectiveness of the compound, wherein at least one adverse effect of a disorder is ameliorated or alleviated. More specifically, administering a compound or composition results in complete or at least partial inhibition of a metabolic pathway or other biological processes in a pathogen. In addition, an effective amount is sufficient to result in at least some degree of alleviation or prevention of an infection caused by a pathogen, or prevention of an infection by the pathogen.

The terms "treating or preventing" are intended to include preventing, eradicating, or inhibiting the resulting increase of undesired physiological activity associated with a disorder or infection, for example, in the context of the therapeutic or prophylactic methods of the invention. In another embodiment, the term treating or preventing includes antagonistic effects, e.g., diminishment of the activity or production of mediators of a disorder.

As used herein and unless otherwise indicated, the term "formulation" refers to a composition comprising a compound of the present disclosure that is described in a particular dosage form (e.g., tablet) or with a particular dosage amount.

When administered to a subject (e.g., to an animal for veterinary use or to a human for clinical use), the compounds of the invention can be optionally administered in isolated form.

The phrase "pharmaceutically acceptable salt(s)," as used herein includes but is not limited to salts of acidic or basic groups that may be present in compounds of the present disclosure. Compounds in the present disclosure that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds in the present disclosure that include an amino moiety may form pharmaceutically acceptable salts with various amino acids, in addition to the acids mentioned above. Compounds in the present disclosure that are acidic in nature are capable of forming base salts with various pharmacologically acceptable cations. Examples of such salts include alkali metal or alkaline earth metal salts and ammonium salts, for example, calcium, magnesium, sodium, potassium, lithium, zinc, potassium, and iron salts.

The phrase "pharmaceutically acceptable excipient" may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Remington: The Science and Practice of Pharmacy, 21st Ed. (Lippincott Williams & Wilkins, Baltimore, MD, 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners.

The therapeutic methods provided herein comprise administering a compound of Formula (I) to a subject in an amount which is effective to achieve its intended purpose. While individual needs vary, determination of optimal ranges of effective amounts of each component is within the skill of the art. Typically, a compound of Formula (I) is administered in an amount from about 0.05 mg/kg to about 500 mg/kg, about 0.05 mg/kg to about 100 mg/kg, about 0.05 mg/kg to about 50 mg/kg, or about 0.05 mg/kg to about 10 mg/kg. In one embodiment, a compound of Formula (I) is administered in an amount from 0.1 mg/kg of body weight of the subject to 300 mg/kg of body weight of the subject. The dosage of a composition can be at any dosage including, but not limited to, about 0.05 mg/week to about 100 mg/week. Particular doses include 0.05, 1, 2, 5, 10, 20, 500, and 100 mg/kg once daily, or once weekly. In one embodiment, a compound of Formula (I) is administered one, two, three, four, or five times a week, i.e., a compound of Formula (I) is administered according to an intermittent dosing schedule. These dosages are exemplary, but there can be individual instances in which higher or lower dosages are merited, and such are within the scope of this disclosure. In practice, the physician or veterinarian determines the actual dosing regimen that is most suitable for an individual subject, which can vary with the age, weight, and response of the particular subject.

The unit oral dose of a compound of Formula (I) may comprise from about 0.01 to about 1000 mg, e.g., about 0.01 to about 100 mg of a compound of Formula (I). In one embodiment, the unit oral dose of a compound of Formula (I) is 0.05 mg, 1 mg, 3 mg, 5 mg, 7 mg, 9 mg, 10 mg 12 mg, 14 mg, 15 mg, 17 mg, 20 mg, 22 mg, 25 mg, 27 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg. The unit dose may be administered one or more times daily, e.g., as one or more tablets or capsules. The unit does may also be administered by IV or subcutaneously to the subject. In practice, the physician or veterinarian determines the actual dosing regimen that is most suitable for an individual subject, which can vary with the age, weight, and response of the particular subject.

In addition to administering a compound of Formula (I) as a raw chemical, it may be administered as part of a pharmaceutical preparation, composition, or formulation. In some embodiments, the pharmaceutical preparation or composition can include one or more pharmaceutically acceptable carriers, excipients, and/or auxiliaries. In some embodiments, the one or more carriers, excipients, and auxiliaries facilitate processing of a compound of Formula (I) into a preparation or composition which can be used pharmaceutically. The preparations, particularly those preparations which can be administered orally, subcutaneously, or topically, and which can be used for one type of administration, such as tablets, dragees, slow release lozenges and capsules, mouth rinses and mouth washes, gels, liquid suspensions, hair rinses, hair gels, and shampoos, and also preparations which can be administered rectally, such as suppositories, as well as suitable solutions for administration by intravenous infusion, subcutaneous injection, topically or orally, contain from about 0.01 to 99 percent, in one embodiment from about 0.25 to 75 percent of active compound(s), together with the one or more carriers, excipients, and/or auxiliaries.

The compounds and pharmaceutical compositions provided herein may be administered to any subject which may experience the beneficial effects of a compound of Formula (I). Foremost among such subjects are veterinary animals (cows, sheep, pigs, horses, dogs, cats and the like) although the methods and compositions provided herein are not intended to be so limited. Other subjects include humans. In one embodiment, the subject is a veterinary animal having a microbial infection caused by one or more eukaryotic pathogens. In another embodiment, the subject is a veterinary animal having a Staphylococcal infection.

The pharmaceutical preparations provided herein are manufactured by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

In the present disclosure, the term "halo" or "halogen" as used by itself or as part of another group refers to —Cl, —F, —Br, or —I. In one embodiment, the halo is —Cl or —F. In one embodiment, the halo is —Cl.

In the present disclosure, the term "nitro" as used by itself or as part of another group refers to —$NO_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_1$-3 alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

In the present disclosure, the term "optionally substituted cycloalkyl" as used herein by itself or as part of another group means that the cycloalkyl as defined above is either unsubstituted or substituted with one to three substituents independently selected from the group consisting of halogen, hydroxy, nitro, cyano, —$SCH_3$, —$SCF_3$, —$NR_{10}R_{11}$, —$C(=O)NR_{10}R_{11}$, —$C(=O)R_{13}$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-12}$ cycloalkyl, optionally substituted $C_6$-$C_{14}$ aryl, optionally substituted 5- to 14-membered heteroaryl, and optionally substituted 3- to 14-membered heterocyclic ring, wherein $R_{10}$ and $R_{11}$ are independently selected from the group consisting of hydrogen and $C_{1-6}$ alkyl; or $R_{10}$ and $R_{11}$ taken together with the nitrogen atom to which they are attached form a 3- to 12-membered heterocyclic ring; and $R_{13}$ is $C_{1-4}$ alkyl.

In the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means that the alkenyl as defined above is either unsubstituted or substituted with one to three substituents independently selected from the group consisting of halogen, hydroxy, nitro, cyano, —$SCH_3$, —$SCF_3$, —$NR_{10}R_{11}$, —$C(=O)NR_{10}R_{11}$, —$C(=O)R_{13}$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-12}$ cycloalkyl, optionally substituted $C_6$-$C_{14}$ aryl, optionally substituted 5- to 14-membered heteroaryl, and optionally substituted 3- to 14-membered heterocyclic ring, wherein $R_{10}$ and $R_{11}$ are independently selected from the group consisting of hydrogen and $C_{1-6}$ alkyl; or $R_{10}$ and $R_{11}$ taken together with the nitrogen atom to which they are attached form a 3- to 12-membered heterocyclic ring; and $R_{13}$ is $C_{1-4}$ alkyl.

In the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups. In the present disclosure, the term "optionally substituted alkynyl" as used herein by itself or as part of another group means that the alkynyl as defined above is either unsubstituted or substituted with one to three substituents independently selected from the group consisting of halogen, hydroxy, nitro, cyano, —$SCH_3$, —$SCF_3$, —$NR_{10}R_{11}$, —$C(=O)NR_{10}R_{11}$, —$C(=O)R_{13}$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-12}$ cycloalkyl, optionally substituted $C_6$-$C_{14}$ aryl, optionally substituted 5- to 14-membered heteroaryl, and optionally substituted 3- to 14-membered heterocyclic ring, wherein $R_{10}$ and $R_{11}$ are independently selected from the group consisting of hydrogen and $C_{1-6}$ alkyl; or $R_{10}$ and $R_{11}$ taken together with the nitrogen atom to which they are attached form a 3- to 12-membered heterocyclic ring; and $R_{13}$ is $C_{1-4}$ alkyl.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-6}$ haloalkyl group. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-6}$ alkoxy group. In another embodiment, the alkoxy group is chosen from a $C_{1-4}$ alkyl attached to a terminal oxygen atom, e.g., methoxy, ethoxy, and tert-butoxy.

In the present disclosure, the term "haloalkoxy" as used by itself or as part of another group refers to a $C_{1-4}$ haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic, bicyclic, or tricyclic aromatic ring system having from six to fourteen carbon atoms, i.e., $C_6$-$C_{14}$ aryl. Non-limiting exemplary aryl groups include phenyl (abbreviated as "Ph"), 1-naphthyl, 2-naphthyl, phenanthryl, anthracyl, indenyl, azulenyl, biphenyl, biphenylenyl, and fluorenyl groups. In one embodiment, the aryl group is chosen from phenyl, 1-naphthyl, or 2-naphthyl. In one embodiment, the aryl is a bicyclic or tricyclic $C_{10}$-$C_{14}$ aromatic ring system.

In the present disclosure, the term "optionally substituted aryl" as used herein by itself or as part of another group means that the aryl as defined above is either unsubstituted or substituted with one to five substituents independently selected from the group consisting of halogen, hydroxy, nitro, cyano, —$SCH_3$, —$SCF_3$, —$NR_{10}R_{11}$, —$C(=O)NR_{10}R_{11}$, —$C(=O)R_{13}$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-12}$ cycloalkyl, optionally substituted $C_6$-$C_{14}$ aryl, optionally substituted 5- to 14-membered heteroaryl, and optionally substituted 3- to 14-membered heterocyclic ring, wherein $R_{10}$ and $R_{11}$ are independently selected from the group consisting of hydrogen and $C_{1-6}$ alkyl; or $R_{10}$ and $R_{11}$ taken together with the nitrogen atom to which they are attached form a 3- to 12-membered heterocyclic ring; and $R_{13}$ is $C_{1-4}$ alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl, 3,4-di-chlorophenyl, 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclic rings. Non-limiting examples include:

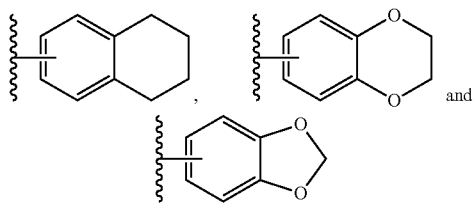

The terms "aralkyl" as used herein by itself or as part of another group refers to an alkyl substituted with one or two optionally substituted aryl groups. In one embodiment, the alkyl is substituted with one optionally substituted aryl group. In one embodiment, the aryl is an optionally substituted phenyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the alkyl is a $C_3$ alkyl. Non-limiting exemplary (aryl)alkyl groups include benzyl, phenethyl, phenpropyl, and —$CHPh_2$.

The embodiments illustrated and discussed above and in the following Examples section are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

EXAMPLES

Example 1

Compound Synthesis

Compounds of Formula (I) were prepared as described in WO 2019/005982.

Example 2

Activity of Compounds Against *Staphylococcus* sp

The growth inhibition of compounds of Formula (I) were evaluated against the following *Staphylococcus* sp. bacteria strains: *S. schleiferi* (S.s), *S. pseudintermedius* (S.p.), *S. chromogenes* (S.c), and *S. aureus* (S.a).

Growth Inhibition of *Staphylococcus* Species Assay Description

Overnight cultures were diluted 1:200 in LB media and grown at 37° C. until the mid-logarithmic phase ($OD_{600}$=0.5-0.8). Cultures were diluted in a 96-well plate to $1\times10^5$ in 150 μL LB media and treated with inhibitors at concentrations ranging from 2 nM to 100 μM. Bacteria were grown at 37°C for 20 h with cyclic shaking at 700 rpm in a FLUOstar Omega microplate reader (BMG Labtech). Growth was assessed over 20 h by measuring the $OD_{600}$ at 20 min increments. The half-maximal inhibitory concentration ($IC_{50}$) values were determined during logarithmic growth using GraphPad Prism software. All experiments were performed at least in triplicate and data reported represent the mean±SEM. See Edwards et al., "Potent, specific MEPicides for treatment of zoonotic staphylococci," BioRxiv 2019.

Minimum Bactericidal (MBC) Assay

Overnight cultures were diluted 1:200 in LB media and grown at 37° C. until reaching mid-logarithmic phase of growth. Compounds were added to cultures at their respective $IC_{50}$ and at $10\times IC_{50}$, and the bacteria were incubated at 37° C. for 24 h while shaking. Cultures were serially diluted in Dulbecco's Phosphate Buffered Saline (PBS; Gibco) and plated on LB agar. Colonies were enumerated after overnight growth at 37° C. Values reflect the mean and standard deviations of at least three independent experiments. See Edwards et al., "Potent, specific MEPicides for treatment of zoonotic staphylococci," BioRxiv 2019.

The results of the growth inhibition and MBC assays are shown in Table 2 and FIG. 1. The activity of fosmidomycin (FSM) and FR-900098 is provided for comparison.

TABLE 2

| Formula | ID | Bacterial $IC_{50}$ μM (Mean ± SD) | | | |
| --- | --- | --- | --- | --- | --- |
| | | S.s. | S.p. | S.c. | S.a. |
| | fosmidomycin | 0.78 ± 0.13 | 0.31 ± 0.04 | 0.31 ± 0.01 | >100 |
| II | RCB-185 | 0.10 ± 0.01 | 0.26 ± 0.03 | 0.07 ± 0.02 | >100 |
| III | ERJ-207 | 55.50 ± 2.41 | 57.07 ± 51.86 | 53.8 ± 4.8 | >100 |
| IV | FR-900098 | 41.06 ± 6.65 | 34.14 ± 6.54 | 17.3 ± 3.43 | >100 |
| V | JXW-572 | 4.17 ± 0.47 | 4.31 ± 0.51 | 1.13 ± 0.34 | >100 |
| VI | JXW-573 | 0.03 ± 0.00 | 0.21 ± 0.04 | 0.04 ± 0.00 | >90 |
| VII | KMH-102 | 0.21 ± 0.05 | | | |
| VIII | JXW-189 | 1.3 | | | |
| IX | JXW-168 | 8.7 | | | |
| XVIII | RC-072 | 2.5 | | | |

Example 3

Activity of Compounds Against Recombinant DXR Enzymes

The activity of compounds of Formula (I) were evaluated against recombinant DXR enzymes. The results for representative compounds of Formula (I) are shown in Table 3 (n=3). The activity of fosmidomycin (FSM) and FR-900098 is provided for comparison.

DXR Enzyme Activity Assay Description.

Oxidation of NADPH to $NADP^+$ as a result of substrate turnover was monitored at 340 nm in a POLARstar Omega microplate reader (BMG Labtech). The standard reaction had a final concentration of 62.5 nM purified DXR protein, 0.5 mM NADPH, 100 mM NaCl, 25 mM Tris pH 7.5, 10% glycerol, 1 mM $MgCl_2$ and 0.09 mg/mL BSA in 50 µL volume per assay. Reactions were initiated by the addition of DOXP after 15 min incubation of the reaction mixture without DOXP at 37° C. Absorption at 340 nm was measured continuously for up to 45 min. For $K_m$ [DOXP] determination, DOXP concentrations between 0 and 2 mM were tested at 0.5 mM NADPH. The linear range of enzyme activity was determined by varying the DXR concentration at 1 mM DOXP and 1 mM NADPH. $IC_{50}$ assays were performed using the standard reaction conditions with the respective amount of DXR inhibitor added to obtain the given final concentrations. Data points from at least three independent replicates were analyzed by nonlinear regression using GraphPad Prism software. Slopes of changing absorbance values were converted to (µM DOXP)(mg enzyme)$^{-1}$ s$^{-1}$ using a NADPH standard curve (data not shown). For the determination of the inhibitory constant Ki [FSM] of DXR, enzyme activity over a range of DOXP substrate concentrations between 0 and 2 mM was measured for FSM between 0 mM to 4 mM. Data points from at least three independent replicates were analyzed as described above. See Edwards et al., "Potent, specific MEPicides for treatment of zoonotic staphylococci," BioRxiv 2019.

TABLE 3

| Structure | Compound | S. chromogenes $IC_{50}$ µM (mean ± SD) | S. schleiferi $IC_{50}$ µM (mean ± SD) |
|---|---|---|---|
| 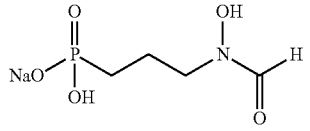 | Fosmidomycin | 0.34 ± 0.08 | 0.67 ± 0.06 |
| 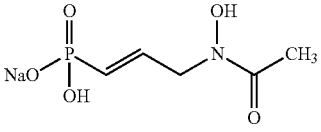 | ERJ-207 | 1.69 ± 0.45 | 3.31 ± 1.02 |
| 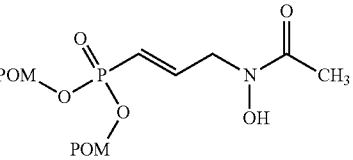 | RCB-185 | >100 | >100 |
| 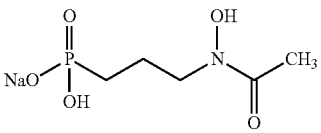 | FR-900098 | 0.36 ± 0.12 | 1.00 ± 0.18 |
| 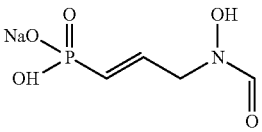 | JXW-572 | 0.17 ± 0.02 | 0.41 ± 0.11 |
| 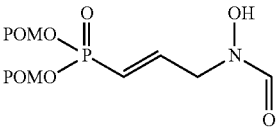 | JXW-573 | 15.24 ± 2.36 | 12.56 ± 1.88 |

Example 4

Metabolite Analysis of *Staphylococcus* pseudintermedius

Targeted metabolic profiling of MEP pathway intermediates in *S. pseudintermedius* was conducted. The results are shown in FIGS. 2-7. See Wang and Dowd, ACS Infect Dis. 4(3):278-290 (2018).

Sample Preparation for Mass Spectrometry Analysis

Overnight cultures of *Staphylococcus* spp. were diluted 1:200 in LB media and grown at 37° C. until reaching mid-logarithmic phase. Cultures were then treated for 2 h with FSM at 10× their $IC_{50}$ while shaking at 37° C. For normalization, the $OD_{600}$ was determined after 2 h of treatment with the DXR inhibitors. Cells were pelleted by centrifugation for 5 min at 3000×g at 4° C. The supernatants were removed and cells were washed twice with PBS (Gibco). The supernatants were removed and the pellets stored at −80° ° C. until analysis. MEP intermediates were extracted from the samples using glass beads (212-300 u) and 600 µL chilled $H_2O$: chloroform:methanol (3:5:12 v/v) spiked with PIPES (piperazine-N,N'-bis(2-ethanesulfonic acid) as internal standard. The cells were disrupted with the TissueLyser II instrument (Qiagen) using a microcentrifuge tube adaptor set pre-chilled for 2 min at 20 Hz. The samples were then centrifuged at 16,000×g at 4° ° C. for 10 min, the supernatants collected, and pellet extraction repeated once more. The supernatants were pooled and 300 µL chloroform and 450 µL of chilled water were added to the supernatants. The tubes were vortexed and centrifuged. The upper layer was transferred to a 2 mL tube PVDF filter (ThermoFisher, F2520-5) and centrifuged for 5 min at 4,000×g at 4° C. The samples were transferred to new tubes and dried using a speed-vac. The pellets were re-dissolved in 100 µL of 50% acetonitrile.

LC-MS/MS Analysis

For LC separation, Luna-NH2 column (3 µm, 150×2 mm, Phenomenex) was used flowing at 0.4 mL/min. The gradient of the mobile phases A (20 mM ammonium acetate, pH 9.8, 5% acetonitrile) and B (100% acetonitrile) was as follows: 60% B for 1 min, to 6% B in 3 min, hold at 6% B for 5 min, then back to 60% B for 0.5 min. The LC system was interfaced with a Sciex QTRAP 6500$^+$ mass spectrometer equipped with a TurboIonSpray (TIS) electrospray ion source. Analyst software (version 1.6.3) was used to control sample acquisition and data analysis. The QTRAP 6500$^+$ mass spectrometer was tuned and calibrated according to the manufacturer's recommendations. The metabolites were detected using MRM transitions that were previously optimized using standards. The instrument was set-up to acquire in negative mode. For quantification, an external standard curve was prepared using a series of standard samples containing different concentrations of metabolites and a fixed concentration of the internal standard. The limit of detection for 1-deoxy-D-xylulose 5-phosphate (DOXP), 4-diphosphocytidyl-2-C-methylerythritol (CDP-ME), and 2-C-methyl-D-erythritol 2,4-cyclopyrophosphate (MEcPP) was 0.0064 µM for a 10 µL injection volume. Data reflect the mean and SD of at least three independent experiments. T-tests were used to test for significance between untreated (UNT) and drug-treated bacteria (Prism). See Edwards et al., "Potent, specific MEPicides for treatment of zoonotic staphylococci," BioRxiv 2019.

Example 5

Carotenoid Extraction and Analysis

Figure 8:
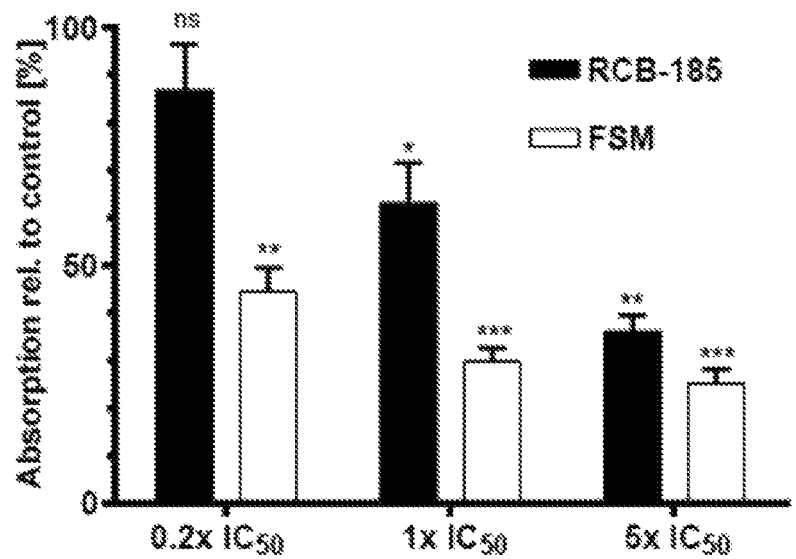
FIG. 8 is bar graph showing the carotenoid analysis of FSM and RCB-185 at the concentrations indicated.

Mid-logarithmic phase cultures were treated with inhibitors at the IC$_{50}$, 0.2*IC$_{50}$, and 5*IC$_{50}$, and then incubated at 37° C. for 24 h while shaking. Subsequently, 5 mL of samples were diluted to 3.2×10$^9$ CFU/mL and cells were pelleted by centrifugation for 1 min at 10,000×g. Pellets were washed with deionized water and resuspended in 1 mL methanol. Samples were incubated at 55° C. for 3 min, centrifuged at 15,000×g for 1 min, and the supernatants measured photometrically at 465 nm. The data represent the mean±SD from at least three independent experiments. One-way ANOVA was used to test for significance between the treatment groups and an untreated control (VassarStats). The results are shown in FIG. 8.

Having now fully described the compounds, compositions, and herein, it will be understood by those of skill in the art that the same can be performed within a wide and equivalent range of conditions, formulations, and other parameters without affecting the scope of the methods, compounds, and compositions provided herein or any embodiment thereof. All patents, patent applications, and publications cited herein are fully incorporated by reference herein in their entirety.

We claim:

1. A method for treating a Staphylococcal infection in a subject in need thereof, the method comprising administering to the subject an effective amount of a compound of Formula (XVIII):

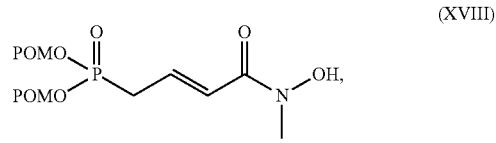

or a pharmaceutically acceptable salt thereof, wherein POM is —CH$_2$OC(=O)C(CH$_3$)$_3$.

2. The method of claim 1, wherein the subject is a companion animal.

3. The method of claim 2, wherein the companion animal is a dog or cat.

4. The method of claim 1, wherein the subject is a farm animal.

5. The method of claim 4, wherein the farm animal is a cow.

* * * * *